(12) United States Patent
Gulyas et al.

(10) Patent No.: US 8,716,503 B2
(45) Date of Patent: May 6, 2014

(54) PROCESS FOR PREPARING DIVINYLARENE DIOXIDES

(75) Inventors: Gyongyi Gulyas, Lake Jackson, TX (US); Ashwin R. Bharadwaj, Pearland, TX (US); Robert J. Wright, Houston, TX (US); Marty J. Null, Lake Jackson, TX (US); Eric B. Ripplinger, Lake Jackson, TX (US)

(73) Assignee: Dow Global Technologies LLC, Midland, MI (US)

( * ) Notice: Subject to any disclaimer, the term of this patent is extended or adjusted under 35 U.S.C. 154(b) by 0 days.

(21) Appl. No.: 13/498,402

(22) PCT Filed: Oct. 15, 2010

(86) PCT No.: PCT/US2010/052766
§ 371 (c)(1),
(2), (4) Date: Mar. 27, 2012

(87) PCT Pub. No.: WO2011/056381
PCT Pub. Date: May 12, 2011

(65) Prior Publication Data
US 2012/0209015 A1    Aug. 16, 2012

Related U.S. Application Data

(60) Provisional application No. 61/258,072, filed on Nov. 4, 2009.

(51) Int. Cl.
*C07D 301/06* (2006.01)
*C07D 301/12* (2006.01)

(52) U.S. Cl.
USPC .......................................... 549/533; 549/531

(58) Field of Classification Search
USPC ............................................... 549/531, 533
See application file for complete search history.

(56) References Cited

U.S. PATENT DOCUMENTS

| 2,982,752 | A | 5/1961 | Phillips et al. |
| 3,442,912 | A | 5/1969 | Hatch et al. |
| 5,962,547 | A | 10/1999 | Nikolic et al. |

FOREIGN PATENT DOCUMENTS

| EP | 94726 | 1/1986 |
| GB | 843083 | 12/1958 |
| JP | 09286750 | 11/1997 |

OTHER PUBLICATIONS

Inoue et al., Effect of Anions of the Epoxidation of Styrenes with H2O2 in the Presence of Ammonium Heplamolybdate (VI)-Dioctyllin Oxide Catalysts, Bulletin of the Chemical Society of Japan, 1991, 3442-3444, 64, Japan.
Worzakowska, Influence of Cure Schedule on on the Viscoelastic Properties and Thermal Degradation of Crosslinked Mono-and Diepoxides Obtained During the Reaction of Hydrogen Peroxide and Divinylbenzene, Journal of Applied Polymer Science, 2007, 462-469, Lupin, Poland.
Ruggli et al., Kondensatianen mit Isophtalaldehyd und Terephlalaldehyd, Helvetica Cheimca Acta, 1940, 718-725, 23. Only in German—No English Abstract.
Hopff et al., Zur Kenntnis der aromatischen Di-und Triepoxyde, Helvetica Chemica Acta, 1957, 274-283, 40 (2)—Only in German—No English Abstract.
Corey et al., Dimethylsulloxonium Methylide, Journal of the American Chemical Society, 1962, 867-868, 84 (5).
Laue et al., Named Organic Reactions, John Wiley & Sons, Ltd., 2005, 254-258, ed. 2, Wolfsburg, Germany.
Gorla et al., Synthesis of an Optically Active Platinum (II) Complex Containing a New Terdenlate P-C-P Ligand and Its Catalytic Activity in the Asymmetric Aldal Reaction of Methyl Isocyanoacelale. X-ray Crystal Structure of [2,6-Bis[(1'S,2'S)-1'-(diphenylphosphino)-2',3-O-isopropylidene-2',3'-dihydroxyphopyl]phenyl](n1-nitrato)platinum(II), Organometallics, 1994, 1607-1616, 13.
Payne et al,. Alkali-Catalyzed Epoxidation and Oxidation Using a Nitrile as Co-reactant, Reactions of Hydrogen Peroxide. VII., 1960, 659-663.

*Primary Examiner* — Taylor Victor Oh

(57) ABSTRACT

A process for preparing a divinylarene dioxide including reacting (a) at least one divinylarene with (b) at least one oxidant in the presence of (c) at least one transition metal complex catalyst, and (d) optionally, in the presence of a solvent, and (e) optionally in the presence of a catalyst modifier under conditions to form a divinylarene dioxide product.

17 Claims, No Drawings

PROCESS FOR PREPARING DIVINYLARENE DIOXIDES

CROSS REFERENCE TO RELATED APPLICATIONS

This is a §371 application of PCT International Patent Application Number PCT/US2010/052766 filed Oct. 15, 2010, and claims priority from provisional application Ser. No. 61/258,072, filed Nov. 4, 2009, which is incorporated herein by reference in its entirety.

BACKGROUND OF THE INVENTION

1. Field of the Invention

The present invention is related to a process for preparing divinylarene dioxides, particularly divinylarene dioxides derived from divinylbenzene. More specifically, the present invention relates to a process for preparing a divinylarene dioxide including reacting (a) at least one divinylarene with (b) at least one oxidant in the presence of (c) at least one transition metal complex catalyst.

2. Description of Background and Related Art

Divinylarene dioxides, particularly divinylbenzene dioxide (DVBDO) and others which are derived from divinylbenzene (DVB) are a class, in general, of epoxy resins, in particularly diepoxides. These diepoxides can be used as either reactive diluents or as the main epoxy resin matrix in epoxy thermoset formulations. DVBDO itself has a very low liquid viscosity (for example, a liquid viscosity of less than about 0.02 Pa·s (20 centipoise) making DVBDO especially useful in the preparation of epoxy resin formulations requiring a low viscosity. Epoxy resin formulations made from DVBDO are useful as intermediates for preparing various other products. For example, epoxy resin formulations made from DVBDO are suitable for use in the fields of coatings, composites, and molding compositions.

Heretofore, previously known processes for the preparation of divinylarene dioxides have been unsuccessful in producing a high conversion and a high selectivity of DVBDO. The previously known processes for the preparation of DVBDO typically use hydrogen peroxide ($H_2O_2$) or peracetic acid as the oxidant reactant. For example, the process described in Inoue et. al., Bull. Chem. Soc. Jap., 1991, 64, 3442, employs $H_2O_2$. JP 09286750 discloses a process for producing DVBDO by the epoxidation of DVB using peracetic acid and $H_2O_2$. Another process for preparing DVBDO using peracetic acid is described in U.S. Pat. No. 2,982,752. The above known DVBDO epoxidation processes suffer from various problems including for example, the production of low yields and low selectivities of DVBDO.

Another problem with the processes of the prior art includes the production of undesirable by-products or the formation of side reactions. For example, Worzakowska M, J. Appl. Polym. Sci., 2007, 103, 462 discloses that DVBDO is prepared using a magnesium oxide catalyst in acetonitrile and $H_2O_2$, resulting in the formation of equivalent amount of acetamide by-product and a mixture of mono- and di-epoxides. Ruggli et al., Helvetica Chimica Acta, (1940), 23, 718 describes preparing DVBDO from benzene dialdehyde and diazomethane. Hopff et al., Helvetica Chimica Acta, (1957), 40, 274; and German Patent No. DE 1079614 describes a complicated three-step process for preparing DVBDO by reducing chloroacetylbenzene with lithium aluminum hydride, and subsequently removing HCl from chlorohydrins. Sulfonium ylides for preparing epoxides from carbonyl compounds are described in Corey et al., J. Am. Chem. Soc., 1962, 84 (5), pp. 867-868.

DVBDO is also prepared by treatment of p-terephthaldehyde with trimethylsulfonium chloride yielding p-DVBDO in 50% yield as described in U.S. Pat. No. 3,442,912 and European Patent No. 94726. U.S. Pat. No. 5,962,547 discloses the preparation of DVBDO using potassium persulfate in an acetone-water reaction mixture with no catalyst. No data on product purity or epoxide yield is disclosed in U.S. Pat. No. 5,962,547.

The above processes known in the prior art all suffer, for example, from the disadvantage of generating residual by-products from the oxidizing agent. The residual by-products, such as acids when peracids are the oxidants, or sulfides when sulphonium salts are oxidants, need to be separated from the desired DVBDO product. In addition, the different known preparations usually provide low yields of DVBDO; or if the yield of DVBDO is high, the process requires an inconveniently long reaction time to form the high yields of DVBDO. For example, the reaction time can be as much as 4 days. None of the previously known prior art processes for the preparation of DVBDO can successfully produce DVBDO in high yields (for example greater than 50%) efficiently and economically. In addition, the prior art processes do not produce DVBDO without co-producing undesirable by-products such as acetamide or acetic acid. The acid by-product is especially disadvantageous due to the acid sensitivity of DVBDO.

Accordingly, it is desired to develop a process for successfully preparing a divinylarene dioxide without co-producing undesirable by-products and while the process produces the divinylarene dioxide in high yields economically and efficiently.

SUMMARY OF THE INVENTION

The present invention provides a process for successfully preparing divinylarene dioxides in high yields (e.g. greater than about 50%) without the problems of the prior art processes such as co-production of undesirable acidic by-products.

One embodiment of the present invention is directed to a process for preparing a divinylarene dioxide including reacting (a) at least one divinylarene with (b) at least one oxidant in the presence of (c) at least one transition metal complex catalyst, and (d) optionally, in the presence of a solvent, and (e) optionally in the presence of a catalyst modifier under conditions to form a divinylarene dioxide product.

In a preferred embodiment, the present invention process for producing divinylarene dioxides uses an appropriate oxidant and an appropriate transition metal complex catalyst, such that it is possible to obtain high yields of a divinylarene dioxide with the present invention process. The present invention process is particularly suited for the preparation of divinylbenzene dioxide (DVBDO), a very low viscosity liquid epoxy resin.

Advantageously, the present invention process is carried out under conditions such that the co-production of undesirable by-products is essentially eliminated or at least minimized, for example, to a concentration of less than about 20%. In addition, the process of the present invention advantageously produces divinylarene dioxides in high yields, for example, in yields of greater than about 50%.

DETAILED DESCRIPTION OF THE INVENTION

In its broadest scope, the present invention includes a process for preparing a divinylarene dioxide using an oxidant such as a peroxo compound or a positive oxidation state halogen compound in the presence of a transition metal complex catalyst such as a transition metal Schiff base complex catalyst and optionally in the presence of other additives such as a catalyst modifier and/or a solvent.

Generally, in the process of the present invention, a divinylarene, a transition metal complex catalyst, and optionally an organic solvent and/or optionally any other desirable additives are contacted with an oxidizing agent in a reactor, which may be batch or continuous; and the reactants are allowed to react to produce the corresponding divinylarene dioxide. The co-produced salts, the transition metal complex catalyst, and the optionally-present solvent and catalyst modifier additives may be removed from the divinylarene dioxide product present in the reaction mixture to give a usable divinylarene dioxide product. In turn, the divinylarene dioxide product may optionally be purified, for example, by distillation, crystallization, and other known purification methods known in the art.

As an illustration of one embodiment of the present invention, for example, a divinylarene dioxide such as divinylbenzene dioxide (DVBDO) is prepared by dissolving a divinylbenzene (DVB) in dichloromethane, using an oxidant such as sodium hypochlorite as the oxidizing agent. A transition metal complex catalyst, for example a Mn(III)-Schiff base complex, such as N,N'-bis(3,5-di-tert-butylsalicilidene)-1,2-cyclohexanediamnomanganese(III)chloride may be added to the reaction mixture; and then the reaction may be carried out at a temperature of between about 0° C. to about 100° C. to carry out an epoxidation reaction. After the epoxidation is completed the solvent, organic catalyst modifier and transition metal complex catalyst may be removed from the product; and if desired, the product may be purified by known means such as distillation.

The source of divinylarene useful in the present invention may come from any known sources and particular to known processes for preparing divinylarenes. For example, divinylarenes can be prepared with salt or metal wastes from arenes and ethylene.

In one embodiment of the present invention, the divinylarene useful in the present invention may comprise any substituted or unsubstituted arene nucleus bearing two vinyl groups in any ring position. The arene may include for example benzene, substituted benzenes, or (substituted) ring-annulated benzenes, and mixtures thereof. In one embodiment, divinylbenzene may be ortho, meta, or para isomers or any mixture thereof. Additional substituents may consist of oxidation-resistant groups including for example saturated alkyl, aryl, halogen, nitro, isocyanate, or RO— (where R may be saturated alkyl or aryl), or mixtures thereof. Ring-annulated benzenes may include for example naphthlalene, tetrahydronaphthalene, and the like, and mixtures thereof.

In another embodiment, the divinylarene may contain quantities of substituted arenes. The amount and structure of the substituted arenes depend on the process used in the preparation of the divinylarene. For example, DVB prepared by a known dehydrogenation of diethylbenzene (DEB) may contain ethylvinylbenzene (EVB) and DEB.

The divinylarene used in the process of the present invention may include for example divinylbenzene, divinylnaphthalene, divinylbiphenyl, divinyldiphenylether, and mixtures thereof.

The concentration of the divinylarene used in the present invention may range generally from about 1 weight percent (wt %) to about 100 wt %, preferably from about 5 wt % to about 95 wt %, and more preferably from about 10 wt % to about 90 wt %.

The oxidizing agent or oxidants useful in the present invention may include any oxygen transfer type oxidant well-known in the art, such as for example the compounds under the general classification of (i) peroxo compounds and (ii) positive oxidation state halogen compounds; and mixtures thereof.

The concentration of the oxidant used in the present invention may range generally from about 0.1 wt % to about 100 wt %, preferably from about 2 wt % to about 80 wt %, and more preferably from about 10 wt % to about 50 wt % based on the total weight of the composition.

Generally, examples of the peroxo compounds used as the oxidants in the process of the present invention include compounds with O—O linkages that are capable of losing one oxygen and forming an epoxide with a double bond.

Preferably, the peroxo compounds used as the oxidants in the process of the present invention may include for example peroxocarboxylic acids, peroxosulfates, organic hydroperoxides, and mixtures thereof.

Specific examples of the peroxo compounds include Oxone®; potassium peroxomonsulfate or its ammonium or alkylammonium salts; m-chloro-perbenzoic acid (MCPBA); peracetic acid; tert-butylhydroperoxide; cumene hydroperoxide; and mixtures thereof.

Generally, the positive oxidation state halogen compounds used as the oxidants in the process of the present invention are compounds that contain halogens with an oxidation number of, for example, +1, +3, +5 or +7; and mixtures thereof.

Preferably, compounds belonging to the group of positive oxidation state halogen compounds include for example, hypochlorites and hypobromites (+1); chlorites and bromites (+3); chlorates and bromates (+5); perchlorates, perbromates and periodates (+7); and mixtures thereof.

Specific examples of the positive oxidation state halogen compounds include sodium periodate (+7); sodium hypochlorite (+1); iodosyl benzene (+3); iodosylmesitylene (+3); and mixtures thereof.

The preparation of divinylarene dioxides using positive oxidation state halogen compounds or peroxo compounds is achieved with the use of a catalyst. The catalyst used herein comprises a complex of (i) a chelant and (ii) a transition metal. The catalyst may be referred to herein as a "transition metal complex catalyst."

The chelant or chelating agent component of the transition metal complex catalyst used in the present invention may be based on amine, ether oxygen, hydroxyl or carboxylate donor groups such as for example, porphyrin compounds; phthalocyanines; Schiff bases; polyazamacrocyclic compounds and their derivatives; aromatic N-hetererocyclic compounds and their deriviatives; pyridine carboxylate; 8-hydroxyquinoline; cyclen or cyclam complexes; and mixtures thereof.

The transition metals of the at least one transition metal complex catalyst may include for example iron, manganese, cobalt, nickel, chromium, copper, titanium and mixtures thereof.

Transition metal complex catalyst or the components that make up the transition metal complex catalyst such as the chelant and the transition metal components may be purchased from commercial sources. In an alternative, the transition metal complex catalyst may be prepared by known techniques in the art such as described in Synthetic Communications, 31, 2913, 2001; incorporated herein by reference.

Preferably, the transition metal complex catalyst is selected from one or more of chromium, manganese or nickel Schiff base complexes; manganese or iron porphyrines complexes; iron or manganese aminocarboxylate complexes; iron or manganese cyclen complexes; iron or manganese cyclam complexes; iron or manganese triazacyclononane complexes; iron or manganese pyridine dicarboxylic acid complexes; and mixtures thereof. One preferred embodiment of the transition metal complex catalyst may be a Schiff base complex. The Schiff base complexes originate from two components: the first component may be a salicylic aldehyde and the salicylic aldehyde may be substituted with one or more of the following groups: alkyl, aryl, amino, halogen, nitro group; or a ring-annulated-hydroxy-benzaldehyde and the ring-annulated-hydroxy-benzaldehyde may be substituted with one or more of the following groups: alkyl, aryl, amino, halogen, nitro groups. The second component of the Schiff base complexes may be an amine or a diamine. For example, the amine may be chosen from butylamine, hexylamine, and the like. The diamine may be chosen, for example, from ethylene diamine, o-phenylene diamine, 1,2-cyclohexyl diamine, and the like; and mixtures thereof.

The chemical structures of the possible embodiments of the Schiff base complex catalyst useful in the present invention process may be illustrated as follows:

Structure A

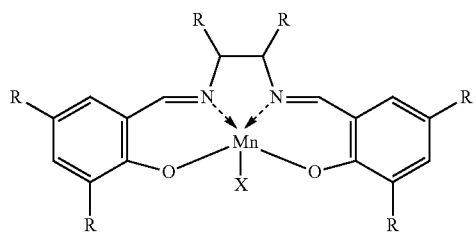

Structure B

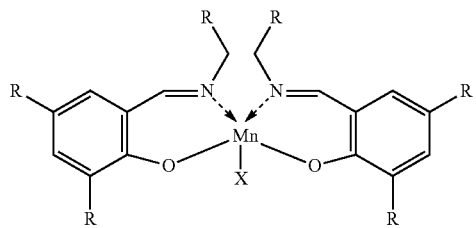

Structure C

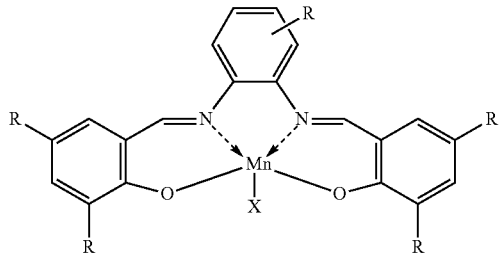

Structure D

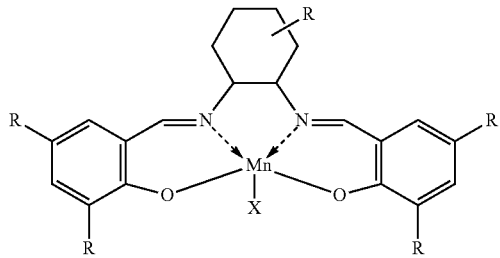

wherein in the above Structures A-D, X is an anion such as halogen, p-tolylsulphonyl, acetate and the like; and R may be alkyl, aryl, ar-alkyl, O-alkyl, O aryl, N-alkyl, N-aryl, alkylamino, hydroxyalkyl, halogen, nitro, hydrogen or any combination thereof.

The concentration of the Schiff base complex catalyst used in the present invention may range generally from about 0.001 wt % to about 15 wt %, preferably from about 0.01 wt % to about 10 wt %, and more preferably from about 0.1 wt % to about 5 wt %.

A solvent may be optionally used in the process of the present invention. The optional solvent useful in the process of the present invention may include for example any inert organic solvent that is inert to the oxidant under the reaction conditions. For example, the solvent may include halogenated alkanes such as dichloromethane; aromatics such as toluene; polar organic solvents such as dimethyl formamide, acetonitrile, or ethers such as tetrahydrofuran; alcohols such as tert-amyl alcohol, tert-butanol, or methanol; fluorinated alcohols such as trifluoroethanol; or mixtures thereof.

The concentration of the solvent used in the present invention may range generally from about 0 wt % to about 99 wt %, preferably from about 10 wt % to about 90 wt %, and more preferably from about 20 wt % to about 80 wt %.

The process of the present invention may use an optional catalyst modifier such as an organic modifier, an inorganic modifier, or mixtures thereof. The organic modifier optionally used in the process of the present invention may include for example Lewis bases such as N-containing heterocyclic compounds such as pyrazole, pyridine, bipyridine, imidazole and their derivatives; N-oxides and alkyl, aryl or cyano-substituted analogs of N-oxides; and mixtures thereof.

The concentration of the organic modifier used in the present invention may range generally from about 0. wt % to about 30 wt %, preferably from about 0.05 wt % to about 20 wt %, and more preferably from about 1 wt % to about 10 wt %.

In another embodiment, the optional inorganic modifier may include for example salts such as sodium or potassium phosphate; sodium or potassium oxalate; sodium or potassium carbonate; sodium or potassium bicarbonate; sodium or potassium acetate, and the like; and mixtures thereof.

The concentration of the inorganic modifier in an aqueous phase used in the present invention may range generally from about 0 wt % to about 50 wt %, preferably from about 0.1 wt % to about 20 wt %, and more preferably from about 1 wt % to about 10 wt %.

In another embodiment of the present invention, the organic and/or inorganic modifier may be added to the reaction composition of the present invention to assist in the reaction process; and subsequently, the modifier may be removed, if desired, after its use.

An assortment of other optional additives may be added to the reaction composition of the present invention including for example, other resins, stabilizers, fillers, plasticizers, catalyst de-activators, and the like; and mixtures thereof.

The concentration of the optional additives used in the present invention may range generally from 0 wt % to about 99.9 wt %, preferably from about 0.1 wt % to about 99.9 wt %, more preferably from about 1 wt % to about 99 wt %, and most preferably from about 2 wt % to about 98 wt %.

The preparation of divinylarene dioxides without co-production of undesirable by-products may be achieved for example by (i) adding to a reactor the following reactants: a divinylarene, a transition metal complex catalyst, optionally an organic modifier, optionally an inorganic modifier and optionally an inert organic solvent; (ii) contacting the reactants with an oxidant; and then (iii) allowing the components in the reaction mixture to react under reaction conditions to produce the corresponding divinylarene dioxide.

The reaction conditions include carrying out the reaction under a temperature, generally in the range of from about 0° C. to about 100° C., preferably from about 5° C. to about 80° C., and more preferably from about 20° C. to about 60° C.

The pressure of the reaction may be generally from about 10.13 kPa to about 1013 kPa (0.1 atmosphere (atm) to about 10 atm).

The reaction process of the present invention may be a batch or a continuous process. The reactor used in the process may be any reactor and ancillary equipment well known to those skilled in the art.

During the reaction for the preparation of divinylarene dioxide, an equivalent amount of sodium chloride by-product may form in the reaction mixture. The formed by-product can be removed from the reaction mixture by separating an organic phase and an aqueous phase formed in the reaction mixture followed by an appropriate number of water washes of the organic phase. One advantage of the present invention process is that other undesirable oxidized by-products and derivatives, such as for example carbonyl compounds and hydrolyzed epoxy products, are not formed in any appreciable quantities using the process of the present invention.

After the reaction of the present invention, the undesirable by-products; and any remaining organic modifier, catalyst, and solvent, may be removed to recover a sufficient amount of usable divinylarene dioxide product. Then the product may optionally be purified by well-known means in the art such as by chromatography, distillation, crystallization, and the like.

One advantage of the present invention process is that high yields of divinylarene dioxides may be produced by the process of the present invention. With high yields of divinylarene dioxides produced, the process of the present invention advantageously requires less recycle and produces less waste.

The "high yield" of divinylarene dioxide produced by the process of the present invention is generally greater than about 30%; and preferably, ranges from about 70% to about 100%; more preferably, from about 80% to about 100%; and most preferably, from about 90% to about 100% based on divinylarene starting material.

The divinylarene dioxides prepared by the process of the present invention, particularly those derived from divinylbenzene such as for example divinylbenzene dioxide (DVBDO), are class of diepoxides which have a relatively low liquid viscosity but a higher rigidity than conventional epoxy resins.

The divinylarene dioxide useful in the present invention may comprise, for example, any substituted or unsubstituted arene nucleus bearing two vinyl groups in any ring position. The arene portion of the divinylarene dioxide may comprise benzene, substituted benzenes, ring-annulated benzenes, substituted ring-annulated benzenes, homologously bonded benzenes, substituted homologously bonded benzenes, or mixtures thereof. The divinylarene portion of the divinylarene dioxide may be ortho, meta, or para isomers or any mixture thereof. Additional substituents may consist of $H_2O_2$-resistant groups including saturated alkyl, aryl, halogen, nitro, isocyanate, or RO— (where R may be a saturated alkyl or aryl). Ring-annulated benzenes may comprise for example naphthlalene, tetrahydronaphthalene, and the like. Homologously bonded (substituted) benzenes may comprise for example biphenyl, diphenylether, and the like.

The divinylarene oxide product prepared by the process of the present invention may be illustrated generally by general chemical Structures I-IV as follows:

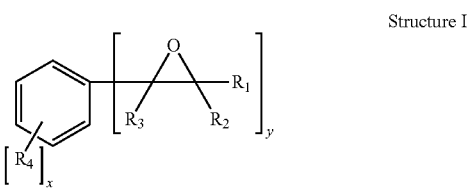

Structure I

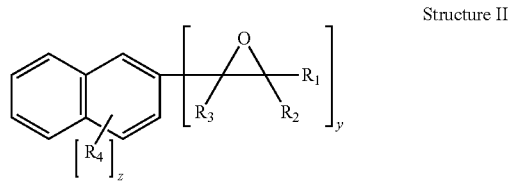

Structure II

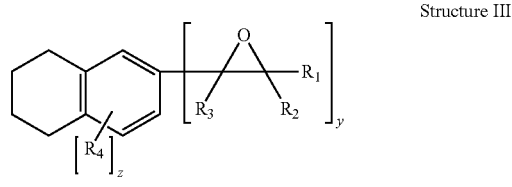

Structure III

In the above Structures I, II, III and IV of the divinylarene dioxide product of the present invention, each $R_1$, $R_2$, $R_3$ and $R_4$ individually may be hydrogen, an alkyl, cycloalkyl, an aryl or an aralkyl group; or a oxidant-resistant group including for example a halogen, a nitro, an isocyanate, or an RO group, wherein R may be an alkyl, aryl or ar alkyl; x may be an integer of 0 to 4; y may be an integer greater than or equal to 2; x+y may be an integer less than or equal to 6; z may be an integer of 0 to 6; and z+y may be an integer less than or equal to 8; and Ar is an arene fragment including for example, 1,3-phenylene group.

The divinylarene dioxide product produced by the process of the present invention may include for example alkyl-vinylarene monoxides depending on the presence of alkylvinylarene in the starting material.

In one embodiment of the present invention, the divinylarene dioxide produced by the process of the present invention may include for example divinylbenzene dioxide, divinylnaphthalene dioxide, divinylbiphenyl dioxide, divinyldiphenylether dioxide, and mixtures thereof.

Structure V below illustrates an embodiment of a preferred chemical structure of a DVBDO useful in the present invention:

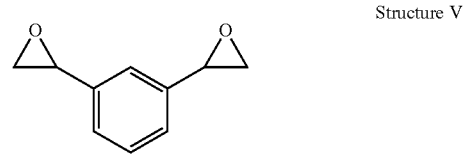 [SMILES: c1cc(C2CO2)cc(C2CO2)c1]

Structure V

Structure VI below illustrates another embodiment of a preferred chemical structure of the DVBDO useful in the present invention:

Structure VI

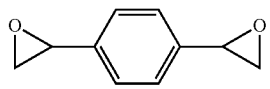

When DVBDO is prepared by the process of the present invention, it is possible to obtain one of three possible isomers: ortho, meta, and para. Accordingly, the present invention includes a DVBDO illustrated by any one of the above Structures individually or as a mixture thereof. Structures V and VI above show the meta (1,3-DVBDO) and para isomers of DVBDO, respectively. The ortho isomer is rare; and usually a mixture of DVBDO is mostly produced as an about 2:1 ratio of meta (Structure V) to para (Structure VI). Thus, the present invention preferably includes as one embodiment a 2:1 ratio of Structure V to Structure VI.

The viscosity of the divinylarene dioxides produced by the process of the present invention ranges generally from about 0.01 Pa·s to about 0.1 Pa·s; preferably, from about 0.01 Pa·s to about 0.05 Pa·s; and more preferably, from about 0.01 Pa·s to about 0.025 Pa·s at 25° C. In one embodiment, the process of the present invention is particularly suited for the preparation of DVBDO, a liquid epoxy resin having a liquid viscosity of less than about 0.02 Pa·s.

The utility of the divinylarene dioxides of the present invention requires thermal stability to allow formulating or processing the divinylarene dioxides at moderate temperatures (for example, at temperatures of from about 100° C. to about 200° C.) for up to several hours (for example, for at least 2 hours or more) without oligomerization or homopolymerization. Oligomerization or homopolymerization during formulation or processing is evident by a substantial increase (e.g., greater than 50 fold) in viscosity or gelling (crosslinking). The divinylarene dioxides of the present invention have sufficient thermal stability such that the divinylarene dioxides do not experience a substantial increase in viscosity or gelling during formulation or processing at the aforementioned moderate temperatures.

The divinylarene dioxide products of the present invention are useful for the preparation of epoxy resin compositions or formulations which, in turn, are useful for preparing thermosets or cured products in the form of coatings, films, adhesives, laminates, composites, electronics, and the like.

EXAMPLES

The following examples and comparative examples further illustrate the present invention in detail but are not to be construed to limit the scope thereof. The product mixtures prepared in the Examples which follow were analyzed by standard gas chromatography (GC) analytical equipment and methods. For each of the following preparations in the Examples, 80% divinylbenzene (DVB) was used containing 20% ethylvinylbenzene (EVB) but the yields and final compositions are referred to DVB. Racemic Schiff base chelants and their Mn-complexes were prepared by the procedures described in Ivica Cepanec et. al., Synthetic Communications, 2001, 31, 2913; and Ana Rosa Silva et. al., New Journal of Chemistry, 2004, 28, 253, each incorporated herein by reference. The reagents: R,R—N,N'-bis(3,5-di-tert-butylsalicilidene)-1,2-cyclohexanediamnomanganese(III)chloride, chiral complex and all other reagents were purchased from Aldrich.

Example 1

Divinylbenzene (DVB) (7.68 mmol, 1.00 g), N,N'-bis-salicilidene-1,2-ethane-diaminomanganese(III)chloride (0.4 mmol, 137 mg) and pyridine N-oxide (1.9 mmol, 137 mg) were transferred into a three neck flask equipped with a dropping funnel and magnetic stirrer. Dichloromethane (10 mL) was added to the flask and stirring was started. The oxidant, sodium hypochlorite (30.7 mmol, 11.9%, 8.3 mL), was delivered dropwise into the resulting solution at 25° C. The resulting reaction mixture was further incubated at this temperature for an additional hour. Then the reaction mixture was filtered, washed three times with brine, and washed twice with NaHSO₃ solution (1M, pH=7), followed by three water washes. The resulting dichloromethane solution was dried over sodium sulfate.

Evaporation to dryness resulted in 0.99 g of product. The product was analyzed by GC analysis. The product DVBDO yield was 97% based on DVB.

Example 2

DVB (1 mmol, 130 mg), R,R—N,N'-bis(3,5-di-tert-butylsalicilidene)-1,2-cyclohexanediamnomanganese(III)chloride (0.05 mmol, 32 mg) and pyridine N-oxide (0.25 mmol, 21 mg) were transferred into a vial equipped with a magnetic stirrer. Dichloromethane (1.00 mL) was added to the vial and stirring was started. The oxidant, sodium hypochlorite (4 mmol, 11.9%, 1.08 mL), was delivered dropwise into the resulting solution at 25° C. The resulting reaction mixture was further incubated at this temperature for 3 hours. Then the resultant organic phase was analyzed by GC. DVBDO yield was 98% based on DVB.

Example 3

DVB (10 mmol, 1.30 g), N,N'-bis(3,5-di-tert-butylsalicilidene)-1,2-cyclohexanediamnomanganese(III)chloride (0.5 mmol, 318 mg) and pyridine N-oxide (2.5 mmol, 238 mg) were transferred into a three neck flask equipped with a condenser, dropping funnel and magnetic stirrer. Dichloromethane (10 mL) was added to the flask and stirring was started. The oxidant, sodium hypochlorite (25 mmol, 11.9%, 12.4 mL), was delivered dropwise into the resulting solution at 25° C. The resulting reaction mixture was further incubated at this temperature for two additional hours. Then the reaction mixture was filtered, washed three times with brine, and washed twice with NaHSO₃ solution (1M, pH=7), followed by three water washes. The resulting dichloromethane solution was dried over sodium sulfate. Evaporation to dryness resulted in 1.87 g product (the transition metal complex catalyst used in this example was not separated). The product was analyzed by GC analysis. The product DVBDO yield was 98%.

Example 4

The DVBDO product prepared in Example 2 was used in this Example 4. Separation of the transition metal complex catalyst, N,N'-bis(3,5-di-tert-butylsalicilidene)-1,2-cyclohexanediaminomanganese(III)chloride, from DVBDO was carried out using column chromatography with a silica gel (Merck 35-70 mesh) stationary phase and a 1.25/1 w/w mixture of dichloroethane and hexane mobile phase. The use of silica gel did not result in a DVBDO loss. The mixture was vacuum distilled. Vacuum distillation resulted in a 10% DVBDO loss; and 95% pure DVBDO and 5% EVBO.

Example 5

DVB (1 mmol, 130 mg); R,R—N,N'-bis(3,5-di-tert-butylsalicilidene)-1,2-cyclohexanediamnomanganese(III)chloride (0.05 mmol, 32 mg); and N-methylmorpholine N-oxide (0.25 mmol, 29 mg) were transferred into a vial equipped with a magnetic stirrer. Dichloromethane (1.00 mL) was added to the vial and stirring was started. The oxidant, sodium hypochlorite (4 mmol, 11.9%, 0.426 mL), was delivered dropwise into the resulting solution at 25° C. The resulting reaction mixture was further incubated at this temperature for an additional hour. Then the resultant organic phase was analyzed by GC. DVBDO yield was 54% based on DVB; and the DVBDO product contained 6% DVBMO.

Example 6

DVB (2 mmol, 260 mg); R,R—N,N'-bis(3,5-di-tert-butyl-salicilidene)-1,2-cyclohexanediamnomanganese(III)chloride (0.05 mmol, 63 mg); and N-methylmorpholine (0.4 mmol, 41 mg) were transferred into a flask equipped with a magnetic stirrer. Dichloromethane (5.00 mL) was added to the flask and stirring was started. The contents of the flask were cooled in an ice bath to 5° C. The oxidant, m-chloroperbenzoic acid (6 mmol, 1.11 g) in dichloromethane solution (20 mL), was delivered dropwise into the resulting solution. The resulting reaction mixture was further incubated at 5° C. for 1 hour. Then the resultant organic phase was poured into a NaHCO$_3$ solution (1M) and stirred at room temperature for 15 minutes. The resultant organic phase was analyzed by GC; and the reaction mixture was found to contain 1% DVB, 21% DVBMO and 66% DVBDO.

Comparative Example A

This Comparative Example A was carried out as described in Example 1 above except that no transition metal complex catalyst was added to the reaction mixture. No epoxide product formation was achieved.

The process of the present invention is not to be limited by the specific examples set forth above including the tables to which they refer. Rather, these examples and the tables they refer to are illustrative of the process of the present invention.

What is claimed is:

1. A process for preparing a divinylarene dioxide comprising reacting (a) at least one divinylarene with (b) at least one oxidant, excluding hydrogen peroxide, in the presence of (c) at least one transition metal complex catalyst under conditions to form a divinylarene dioxide product.

2. A process for preparing a divinylarene dioxide comprising reacting (a) at least one divinylarene with (b) at least one oxidant, excluding hydrogen peroxide, in the presence of (c) at least one transition metal complex catalyst under conditions to form a divinylarene dioxide product; wherein the at least one oxidant comprises an oxygen transfer agent; and wherein the oxygen transfer agent is a positive oxidation state halogen compound or a peroxo compound.

3. The process of claim 2, wherein the positive oxidation state halogen compound is selected from the group consisting of sodium hypochlorite, sodium hypobromide, sodium periodate, iodosylbenzene, iodosyl mesitylene, and mixtures thereof; and wherein the peroxo compound is selected from the group consisting of hydroperoxides, peroxosulfates, peroxocarboxylic acids, and mixtures thereof; or wherein the peroxo compound is selected from the group consisting of m-chloroperbenzoic acid, peracetic acid, potassium peroxomonosulfate or ammonium or phosphonium peroxomonosulfate salts, tert-butylhydroperoxide, cumene hydroperoxide and mixtures thereof.

4. A process for preparing a divinylarene dioxide comprising reacting (a) at least one divinylarene with (b) at least one oxidant, excluding hydrogen peroxide, in the presence of (c) at least one transition metal complex catalyst under conditions to form a divinylarene dioxide product; wherein the at least one divinylarene is divinylbenzene; and wherein the divinylarene dioxide formed is divinylbenzene dioxide.

5. A process for preparing a divinylarene dioxide comprising reacting (a) at least one divinylarene with (b) at least one oxidant, excluding hydrogen peroxide, in the presence of (c) at least one transition metal complex catalyst under conditions to form a divinylarene dioxide product; wherein the reaction is carried out at a temperature within the range of from about 5° C. to about 80° C.

6. The process of claim 2, wherein the at least one transition metal complex catalyst is made up of at least one chelant component and at least one transition metal component; wherein the transition metal component in the transition metal complex catalyst is selected from the group consisting of nickel, chromium, vanadium, iron, manganese, titanium and mixtures thereof; and wherein the chelant component of the transition metal complex catalyst is a Schiff base; wherein the Schiff base is made up of an aldehyde component and an amine component.

7. The process of claim 6, wherein the aldehyde component is selected from the group consisting of salicylic aldehyde, an alkyl, aryl, o-alkyl, O-aryl, N-alkyl, N-aryl, alkylamine, nitro or halogen substituted salicylic aldehyde; a ring annulated hydroxy-benzaldehyde; an alkyl, aryl, o-alkyl, O-aryl, N-alkyl, N-aryl, alkylamine, nitro or halogen substituted ring annulated hydroxy-benzaldehyde; and mixtures thereof; and wherein the amine component is selected from the group consisting of monoamines, alkyl aryl or halogen substituted monoamines; diamines; alkyl aryl or halogen substituted diamines; and mixtures thereof.

8. The process of claim 7, wherein the monoamine is selected from the group consisting of butylamine, hexylamine, and mixtures thereof; and wherein the diamine is selected from the group consisting of ethylene diamine; 1,2 cyclohexyl diamine; 1,2-phenylenediamine; and mixtures thereof.

9. The process of claim 6, wherein the transition metal complex catalyst is immobilized on a solid support; and wherein the solid support is selected from the group consisting of zeolite and silica.

10. The process of claim 2, wherein the concentration of the at least one divinylarene ranges from about 1 weight percent to about 100 weight percent; wherein the concentration of the at least one oxidant ranges from about 0.1 weight percent to about 99 weight percent; and wherein the concentration of the at least one transition metal complex catalyst ranges from about 0.001 weight percent to about 5 weight percent.

11. The process of claim 2, including a solvent, wherein the solvent is selected from the group consisting of a chlorinated hydrocarbon; an aromatic hydrocarbon; a polar solvent; ether; an alcohol; a fluorinated alcohol; and a mixture thereof; and wherein the concentration of said solvent ranges from about 0.1 weight percent to about 99 weight percent.

12. The process of claim 11, wherein the chlorinated hydrocarbon is dichloromethane or dichloroethane; wherein the aromatic hydrocarbon is benzene or toluene; wherein the polar solvent is dimethyl formamide, acetonitrile or acetone; wherein the ether is tetrahydrofuran or dioxane; wherein the alcohol is methanol, tertbutanol, or i-amylalcohol; or wherein the fluorinated alcohol is trifluoroethanol.

13. The process of claim 2, including an organic catalyst modifier; wherein the organic catalyst modifier is a Lewis base; wherein the Lewis base is selected from the group consisting of pyrazole, pyridine, pyrrolidine, bipyridine, imidazole, and mixtures thereof; or wherein the organic catalyst modifier is an N-oxide; wherein the N-oxide is selected from the group consisting of pyridine-N-oxide; N-methylmorpholine-N-oxide; and mixtures thereof.

14. The process of claim 13, wherein the catalyst modifier is immobilized onto a solid support; and wherein the solid support is selected from the group consisting of zeolites and silica.

15. The process of claim 2, including an inorganic catalyst modifier, wherein the catalyst modifier is selected from the group consisting of sodium or potassium phosphate, oxalate, carbonate, bicarbonate, acetate, and mixtures thereof.

16. The process of claim 2, wherein the divinylarene dioxide reaction product is separated from residual transition metal complex catalyst and/or residual catalyst modifier by a separation method; wherein the separation method comprises chromatography, precipitation, extraction, filtration, and/or distillation.

17. The process of claim 2, wherein the divinylarene dioxide reaction product is purified by distillation.

* * * * *